(12) United States Patent
Hull et al.

(10) Patent No.: US 10,281,341 B2
(45) Date of Patent: May 7, 2019

(54) METHODS AND SYSTEMS USING OPTICAL FIBER INTERFEROMETRY

(71) Applicant: Hifi Engineering Inc., Calgary (CA)

(72) Inventors: John Hull, Calgary (CA); Seyed Ehsan Jalilian, Calgary (CA)

(73) Assignee: Hifi Engineering Inc., Calgary, Alberta (CA)

(*) Notice: Subject to any disclaimer, the term of this patent is extended or adjusted under 35 U.S.C. 154(b) by 0 days.

(21) Appl. No.: 15/575,981

(22) PCT Filed: May 19, 2016

(86) PCT No.: PCT/CA2016/050560
§ 371 (c)(1),
(2) Date: Nov. 21, 2017

(87) PCT Pub. No.: WO2016/183677
PCT Pub. Date: Nov. 24, 2016

(65) Prior Publication Data
US 2018/0149528 A1    May 31, 2018

Related U.S. Application Data

(60) Provisional application No. 62/165,073, filed on May 21, 2015.

(51) Int. Cl.
*G01H 9/00*        (2006.01)
*G01K 1/20*        (2006.01)
(Continued)

(52) U.S. Cl.
CPC .......... *G01K 11/32* (2013.01); *G01B 11/161* (2013.01); *G01H 9/004* (2013.01); *G01K 1/20* (2013.01); *G01N 25/16* (2013.01); *G01N 21/45* (2013.01)

(58) Field of Classification Search
CPC ...... G01B 11/161; G01H 9/004; G01K 11/32; G01K 1/20; G01N 21/45; G01N 25/16
See application file for complete search history.

(56) References Cited

U.S. PATENT DOCUMENTS 5,493,390 A * 2/1996 Varasi ............... G01D 5/35383
                                                  250/227.18
6,822,217 B1 * 11/2004 Murgatroyd ............ G01J 3/18
                                                  250/227.14
(Continued)

FOREIGN PATENT DOCUMENTS

EP          0892244 A2    1/1999

OTHER PUBLICATIONS

International Search Report and Written Opinion of the International Searching Authority, dated Aug. 2, 2016, for corresponding International Application No. PCT/CA2016/050560, 10 pages.

*Primary Examiner* — Shawn Decenzo
(74) *Attorney, Agent, or Firm* — Klarquist Sparkmna, LLP

(57) ABSTRACT

Described are methods and systems using optical fiber interferometry to sense interference causing events in a region of interest and differentiate between a strain event and a thermal event. Other methods and systems relate to the use of optical fiber interferometry for determining temperature offset in a region of interest and using the determined temperature offset for determining temperature in the region of interest.

12 Claims, 12 Drawing Sheets

(51) Int. Cl.
*G01B 11/16* (2006.01)
*G01K 11/32* (2006.01)
*G01N 21/45* (2006.01)
*G01N 25/16* (2006.01)

(56) References Cited

U.S. PATENT DOCUMENTS

| | | | | |
|---|---|---|---|---|
| 2002/0176647 | A1* | 11/2002 | Spirin | G01D 5/35303 385/12 |
| 2009/0111417 | A1* | 4/2009 | Waagaard | G01D 5/35303 455/296 |
| 2012/0181420 | A1* | 7/2012 | Duncan | G01V 8/005 250/269.1 |
| 2013/0021615 | A1* | 1/2013 | Duncan | G01H 9/004 356/477 |
| 2017/0074688 | A1* | 3/2017 | Crickmore | G01D 18/00 |
| 2017/0260842 | A1* | 9/2017 | Jin | E21B 43/26 |
| 2018/0045040 | A1* | 2/2018 | Swan | E21B 47/02 |
| 2018/0136058 | A1* | 5/2018 | Singer | G01L 5/166 |

* cited by examiner

METHODS AND SYSTEMS USING OPTICAL FIBER INTERFEROMETRY

CROSS REFERENCE TO RELATED APPLICATIONS

This is the U.S. National Stage of International Application No. PCT/CA2016/050560, filed May 19, 2016, which in turn claims the benefit of U.S. Provisional Application No. 62/165,073, filed May 21, 2015. The provisional application is incorporated herein in its entirety.

TECHNICAL FIELD

The present disclosure is directed at methods and systems using optical fiber interferometry.

BACKGROUND

Optical interferometry is a technique in which two separate light pulses are generated: a sensing pulse and a reference pulse. These pulses may be generated by an optical source such as a laser. When optical interferometry is used for fiber optic sensing applications, the sensing and reference pulses are at least partially reflected back towards an optical receiver and interfere with each other resulting in an interference signal.

In a variety of industries, such as the oil and gas industry, the effect of dynamic strain on various components may be material for determining whether those components are functioning properly and for forecasting the expected life of those components. Dynamic strain may also be monitored for detecting failures in components such as well casing and pipelines. In order to be able to monitor dynamic strain accurately, it would be helpful for an operator to be able to distinguish between a thermal interference causing event and a strain interference causing event.

SUMMARY

According to a first aspect, there is provided a method for using optical fiber interferometry to determine whether an interference causing event comprises a strain event or a thermal event in a region of interest. The method comprises: measuring, in a first zone in the region of interest, a first signal resulting from the interference causing event, wherein the first signal is measured using optical fiber interferometry performed using an optical fiber comprising fiber Bragg gratings (FBGs) that extends through the region of interest and wherein pairs of the FBGs delineate the region of interest into at least the first zone and a second zone having non-overlapping portions; measuring in the second zone a second signal resulting from the interference causing event, wherein the second signal is measured using the optical fiber interferometry performed using the optical fiber; comparing the polarities of the first and second signals; and when the polarities of the first and second signals differ, determining that the interference causing event comprises the strain event.

The method may further comprise determining the product of the first and second signals and determining that the interference causing event comprises the strain event when the product of the first and second signals is negative.

The FBGs may delineate the region of interest into at least three zones, and the first and second zones may be separated by at least another of the zones. The method may further comprise measuring a time of the first and second signals and determining that the interference causing event comprises the thermal event when the times at which the first and second signals are measured differ by more than a strain propagation time. The strain propagation time may comprise a duration of time required by the strain event to propagate through the at least another of the zones separating the first and second zones.

The FBGs may delineate the region of interest into at least three zones, and the first and second zones may be adjacent to each other.

The FBGs may delineate the region of interest into at least three zones, and the method may further comprises: measuring, in each of all remaining zones along the region of interest, additional signals resulting from the interference causing event, wherein each of the additional signals is measured using the optical fiber interferometry performed using the optical fiber; and when the polarities of none of the signals differ, determining that the interference causing event comprises the thermal event.

According to a second aspect, there is provided a method of using optical fiber interferometry to determine temperature offset in a region of interest performed using an optical fiber extending through the region of interest. The optical fiber within the region of interest is within a strain insulating housing and comprises one or more than one pair of fiber Bragg gratings (FBGs) with a fiber segment within the pair of FBGs. Determining the temperature offset comprises: measuring, using the optical fiber interferometry, a signal resulting from a change in optical path length of the fiber segment within the pair of FBGs; and determining the temperature offset from the signal.

The optical fiber extending through the region of interest may comprise at least three FBGs, and the fiber segment between any adjacent two of the FBGs may comprise one sensing zone. Measuring the signal may comprise measuring a different signal from each of the sensing zones. Determining the temperature offset from the signal may comprise determining the temperature offset from an average of the different signals or determining a different temperature offset for each of the sensing zones based on the different signals.

The method may further comprise: measuring a baseline temperature in the region of interest using non-interferometric temperature sensing; and determining the temperature in the region of interest from the measured baseline temperature and the determined temperature offset.

The optical fiber extending through the region of interest may comprise at least three FBGs, and the fiber segment between any adjacent two of the FBGs may comprise one sensing zone. Measuring the signal may comprise measuring a different signal from each of the sensing zones, and determining the temperature offset from the signal may comprise determining a different temperature offset for each of the sensing zones based on the different signals. The method may further comprise: measuring a plurality of different baseline temperatures each of which corresponds to a different one of the sensing zones; and determining a different temperature for each of the sensing zones based on the different baseline temperature and the different temperature offset for each of the different sensing zones.

The non-interferometric temperature sensing may comprise distributed temperature sensing. The non-interferometric temperature sensing may be performed using a thermocouple.

According to another aspect, there is provided a system for determining whether an interference causing event comprises a strain event or a thermal event in a region of interest.

The system comprises: an optical fiber comprising fiber Bragg gratings (FBGs) for extending through the region of interest, wherein pairs of the FBGs delineate the region of interest into at least a first zone and a second zone having non-overlapping portions; an interrogator comprising a laser source and a photodetector, wherein the interrogator is configured to perform optical fiber interferometry by shining laser light along the optical fiber and detecting light reflected by the FBGs; and a controller. The controller is operative to: measure in the first zone a first signal resulting from the interference causing event, wherein the first signal is measured using the optical fiber interferometry; measure in the second zone a second signal resulting from the interference causing event, wherein the second signal is measured using the optical fiber interferometry; compare the polarities of the first and second signals; and determine that the interference causing event comprises the strain event when the polarities of the first and second signals differ.

The controller may be further operative to: determine the product of the first and second signals; and determine that the interference causing event comprises the strain event when the product of the first and second signals is negative.

The FBGs may delineate the region of interest into at least three zones, and the first and second zones may be separated by at least another of the zones. The controller may be further operative to: measure a time of the first and second signals; and determine that the interference causing event comprises the thermal event when the time of the first and second signals differ by more than a strain propagation time, wherein the strain propagation time comprises a duration of time required by the strain event to propagate through the at least another of the zones separating the first and second zones.

The FBGs may delineate the region of interest into at least three zones, and the first and second zones may be adjacent to each other.

The FBGs may delineate the region of interest into at least three zones, and the controller may be further operative to: measure, in each of all remaining zones along the region of interest, additional signals resulting from the interference causing event, wherein each of the additional signals is measured using the optical fiber interferometry; and determine that the interference causing event comprises the thermal event when the polarities of none of the signals differ.

According to another aspect, there is provided a system for determining temperature offset in a region of interest comprising: an optical fiber for extending through the region of interest, the optical fiber comprising a strain insulating housing and one or more than one pair of fiber Bragg gratings (FBGs) with a fiber segment within the pair of FBGs; an interrogator comprising a laser source and a photodetector, wherein the interrogator is configured to perform optical fiber interferometry by shining laser light along the optical fiber and detecting light reflected by the FBGs; and a controller. The controller is operative to: measure, using the optical fiber interferometry, a signal resulting from a change in optical path length of the fiber segment within the pair of FBGs; and determine the temperature offset from the signal.

The optical fiber may comprise at least three FBGs, the fiber segment between any adjacent two of the FBGs may comprise one sensing zone, and the controller may be operative to: measure, using the optical fiber interferometry, a different signal from each of the sensing zones; and determine the temperature offset from an average of the different signals.

The optical fiber may comprise at least three FBGs, the fiber segment between any adjacent two of the FBGs may comprise one sensing zone, and the controller may be operative to: measure, using the optical fiber interferometry, a different signal from each of the sensing zones; and determine a different temperature offset for each of the sensing zones based on the different signals.

The controller may be further operative to determine a temperature in the region of interest from a baseline temperature and the determined temperature offset, and the baseline temperature may be measured in the region of interest using non-interferometric temperature sensing.

The optical fiber may comprise at least three FBGs, the fiber segment between any adjacent two of the FBGs may comprise one sensing zone, and the controller may be operative to: measure, using the optical fiber interferometry, a different signal from each of the sensing zones; determine a different temperature offset for each of the sensing zones based on the different signals; and determine a temperature for each of the sensing zones based on the determined temperature offset for each sensing zone and a baseline temperature for each corresponding sensing zone measured using non-interferometric temperature sensing.

The non-interferometric temperature sensing may comprise distributed temperature sensing. The non-interferometric temperature sensing may be performed using a thermocouple.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more exemplary embodiments.

DETAILED DESCRIPTION

Directional terms such as "top," "bottom," "upwards," "downwards," "vertically," and "laterally" are used in the following description for the purpose of providing relative reference only, and are not intended to suggest any limitations on how any article is to be positioned during use, or to be mounted in an assembly or relative to an environment.

Described herein are embodiments using optical fiber interferometry to sense interference causing events in a region of interest and to differentiate between a strain event and a thermal event. Other embodiments described herein relate to the use of optical fiber interferometry for determining temperature offset in a region of interest and using the determined temperature offset for determining temperature in the region of interest.

Figure 1A:
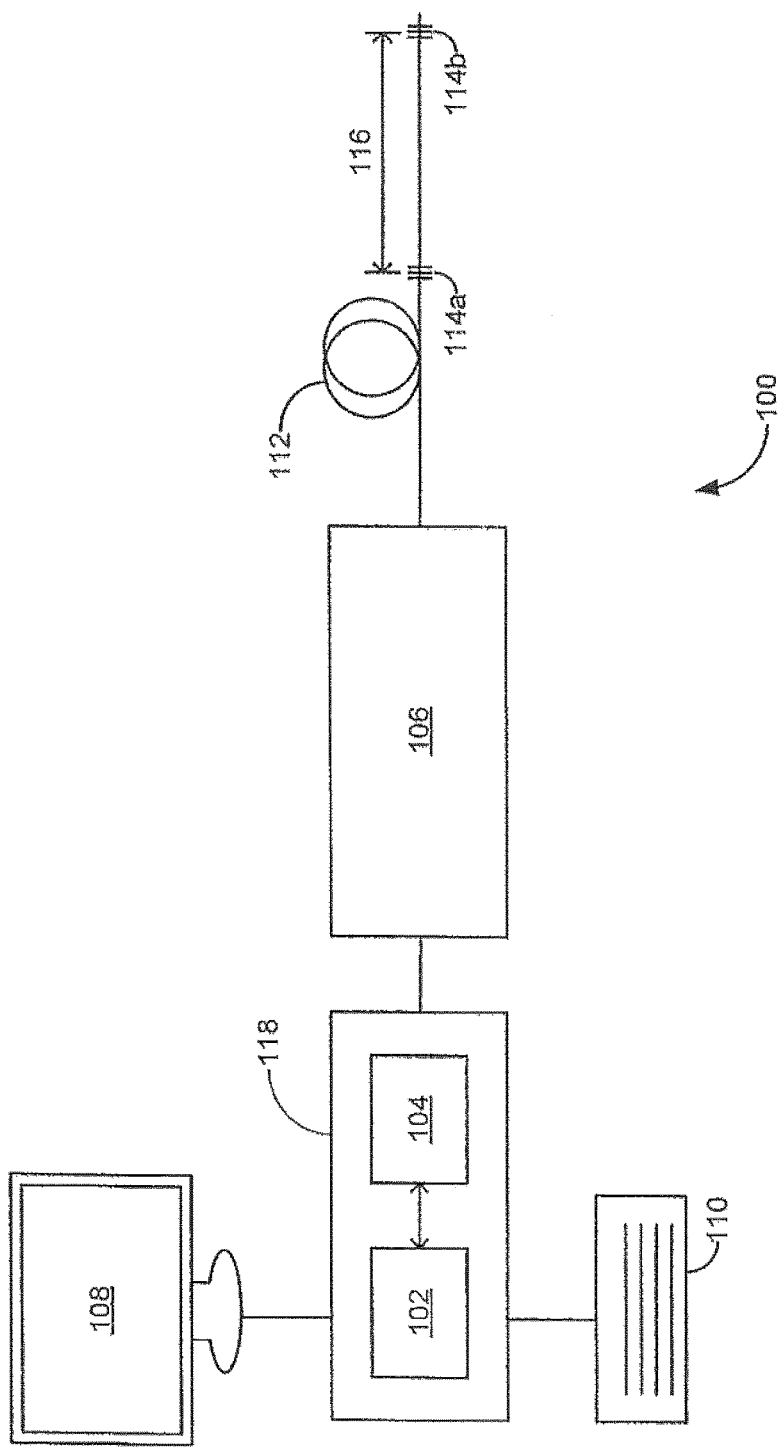
FIG. 1A is a block diagram of a system for fiber optic sensing using optical fiber interferometry, which includes an optical fiber with fiber Bragg gratings ("FBGs") for reflecting a light pulse, according to one embodiment.

Referring now to FIG. 1A, there is shown one embodiment of a system 100 for fiber optic sensing using optical fiber interferometry. The system 100 comprises an optical fiber 112, an interrogator 106 optically coupled to the optical fiber 112, and a signal processing device (controller) 118 that is communicative with the interrogator 106. While not shown in FIG. 1A, within the interrogator 106 are an optical source, optical receiver, and an optical circulator. The optical circulator directs light pulses from the optical source to the optical fiber 112 and directs light pulses received by the interrogator 106 from the optical fiber 112 to the optical receiver.

The optical fiber 112 comprises one or more fiber optic strands, each of which is made from quartz glass (amorphous $SiO_2$). The fiber optic strands are doped with a rare earth compound (such as germanium, praseodymium, or erbium oxides) to alter their refractive indices, although in alternative embodiments the fiber optic strands may not be doped. Single mode and multimode optical strands of fiber are commercially available from, for example, Corning® Optical Fiber. Example optical fibers include ClearCurve™ fibers (bend insensitive), SMF28 series single mode fibers such as SMF-28 ULL fibers or SMF-28e fibers, and InfiniCor® series multimode fibers.

The interrogator 106 generates sensing and reference pulses and outputs the reference pulse after the sensing pulse. The pulses are transmitted along optical fiber 112 that comprises a first pair of fiber Bragg gratings ("FBGs"). The first pair of FBGs comprises first and second FBGs 114a,b (generally, "FBGs 114"). The first and second FBGs 114a,b are separated by a certain segment 116 of the optical fiber 112 ("fiber segment 116"). The length of the fiber segment 116 varies in response to an event (such as a strain event or a thermal event) that the optical fiber 112 experiences.

The light pulses have a wavelength identical or very close to the center wavelength of the FBGs 114, which is the wavelength of light the FBGs 114 are designed to partially reflect; for example, typical FBGs 114 are tuned to reflect light in the 1,000 to 2,000 nm wavelength range. The sensing and reference pulses are accordingly each partially reflected by the FBGs 114a,b and return to the interrogator 106. The delay between transmission of the sensing and reference pulses is such that the reference pulse that reflects off the first FBG 114a (hereinafter the "reflected reference pulse") arrives at the optical receiver 103 simultaneously with the sensing pulse that reflects off the second FBG 114b (hereinafter the "reflected sensing pulse"), which permits optical interference to occur.

While FIG. 1A shows only the one pair of FBGs 114a,b, in alternative embodiments (not depicted) any number of FBGs 114 may be on the fiber 112, and time division multiplexing (TDM) (and optionally, wavelength division multiplexing (WDM)) may be used to simultaneously obtain measurements from them. If two or more pairs of FBGs 114 are used, any one of the pairs may be tuned to reflect a different center wavelength than any other of the pairs. Alternatively a group of multiple FBGs 114 may be tuned to reflect a different center wavelength to another group of multiple FBGs 114 and there may be any number of groups of multiple FBGs extending along the optical fiber 112 with each group of FBGs 114 tuned to reflect a different center wavelength. In these example embodiments where different pairs or group of FBGs 114 are tuned to reflect different center wavelengths to other pairs or groups of FBGs 114, WDM may be used in order to transmit and to receive light from the different pairs or groups of FBGs 114, effectively extending the number of FBG pairs or groups that can be used in series along the optical fiber 112 by reducing the effect of optical loss that otherwise would have resulted from light reflecting from the FBGs 114 located on the fiber 112 nearer to the optical source 101. When different pairs of the FBGs 114 are not tuned to different center wavelengths, TDM is sufficient.

The interrogator 106 emits laser light with a wavelength selected to be identical or sufficiently near the center wavelength of the FBGs 114 that each of the FBGs 114 partially reflects the light back towards the interrogator 106. The timing of the successively transmitted light pulses is such that the light pulses reflected by the first and second FBGs 114a,b interfere with each other at the interrogator 106, and the optical receiver 103 records the resulting interference signal. The event that the fiber segment 116 experiences alters the optical path length between the two FBGs 114 and thus causes a phase difference to arise between the two interfering pulses. The resultant optical power at the optical receiver 103 can be used to determine this phase difference. Consequently, the interference signal that the interrogator 106 receives varies with the event the fiber segment 116 is experiencing, which allows the interrogator 106 to estimate the magnitude of the event the fiber segment 116 experiences from the received optical power. The interrogator 106 digitizes the phase difference ("output signal") whose magnitude and frequency vary directly with the magnitude and frequency of the event the fiber segment 116 experiences.

The signal processing device (controller) 118 is communicatively coupled to the interrogator 106 to receive the output signal. The signal processing device 118 includes a processor 102 and a non-transitory computer readable medium 104 that are communicatively coupled to each other. An input device 110 and a display 108 interact with the processor 102. The computer readable medium 104 has encoded on it statements and instructions to cause the processor 102 to perform any suitable signal processing methods to the output signal. For example, if the fiber segment 116 is laid adjacent a region of interest that is simultaneously experiencing vibration at a rate under 20 Hz and acoustics at a rate over 20 Hz, the fiber segment 116 will experience similar strain and the output signal will comprise a superposition of signals representative of that vibration and those acoustics. The processor 102 may apply a low pass filter with a cutoff frequency of 20 Hz to the output signal to isolate the vibration portion of the output signal from the acoustics portion of the output signal. Analogously, to isolate the acoustics portion of the output signal from the vibration portion, the processor 102 may apply a high pass filter with a cutoff frequency of 20 Hz. The processor 102 may also apply more complex signal processing methods to the output signal; example methods include those described in PCT application PCT/CA2012/000018 (publication number WO 2013/102252), the entirety of which is hereby incorporated by reference.

Figure 1B:
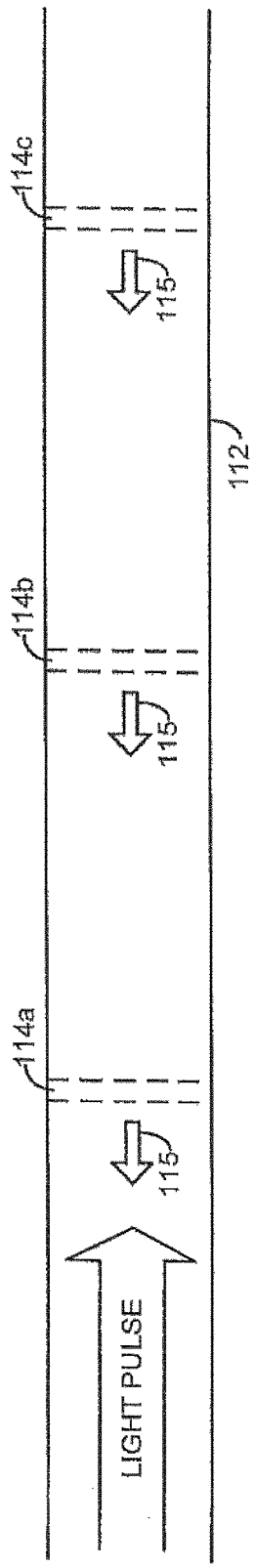
FIG. 1B is a schematic that depicts how the FBGs reflect a light pulse.

FIG. 1B depicts how the FBGs 114 reflect the light pulse, according to another embodiment in which the optical fiber 112 comprises a third FBG 114c. In FIG. 1B, the second FBG 114b is equidistant from each of the first and third FBGs 114a,c when the fiber 112 is not strained. The light pulse is propagating along the fiber 112 and encounters three different FBGs 114, with each of the FBGs 114 reflecting a portion 115 of the pulse back towards the interrogator 106. In embodiments comprising three or more FBGs 114, the portions of the sensing and reference pulses not reflected by the first and second FBGs 114a,b can reflect off the third FBG 114c and any subsequent FBGs 114, resulting in interferometry that can be used to detect an event along the fiber 112 occurring further from the optical source 101 than the second FBG 114b. For example, in the embodiment of FIG. 1B, a portion of the sensing pulse not reflected by the first and second FBGs 114a,b can reflect off the third FBG 114c and a portion of the reference pulse not reflected by the first FBG 114a can reflect off the second FBG 114b, and these reflected pulses can interfere with each other at the interrogator 106.

Any changes to the optical path length of the fiber segment 116 result in a corresponding phase difference between the reflected reference and sensing pulses at the interrogator 106. Since the two reflected pulses are received as one combined interference pulse, the phase difference between them is embedded in the combined signal. This phase information can be extracted using proper signal processing techniques, such as phase demodulation. The relationship between the optical path of the fiber segment 116 and that phase difference (θ) is as follows:

$$\theta = \frac{2\pi nL}{\lambda}$$

where n is the index of refraction of the optical fiber; L is the optical path length of the fiber segment 116; and λ is the wavelength of the optical pulses. A change in nL is caused by the fiber experiencing longitudinal strain induced by energy being transferred into the fiber. The source of this energy may be, for example, an object outside of the fiber experiencing dynamic strain, undergoing vibration, emitting energy or a thermal event. As used herein, "dynamic strain", refers to strain that changes over time. Dynamic strain that has a frequency of between about 5 Hz and about 20 Hz is referred to by persons skilled in the art as "vibration", dynamic strain that has a frequency of greater than about 20 Hz is referred to by persons skilled in the art as "acoustics", and dynamic strain that changes at a rate of <1 Hz, such as at 500 pHz, is referred to as "sub-Hz strain".

Figure 1C:
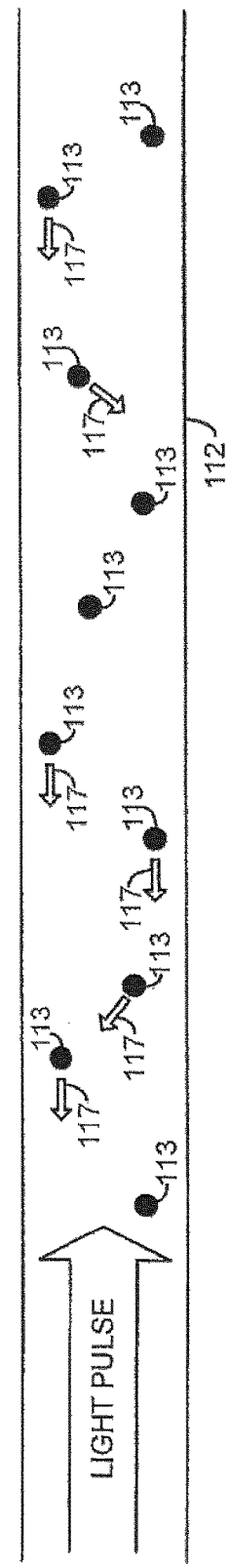
FIG. 1C is a schematic that depicts how a light pulse interacts with impurities in an optical fiber that results in scattered laser light due to Rayleigh scattering, which is used for distributed acoustic sensing ("DAS").
Figure 10:
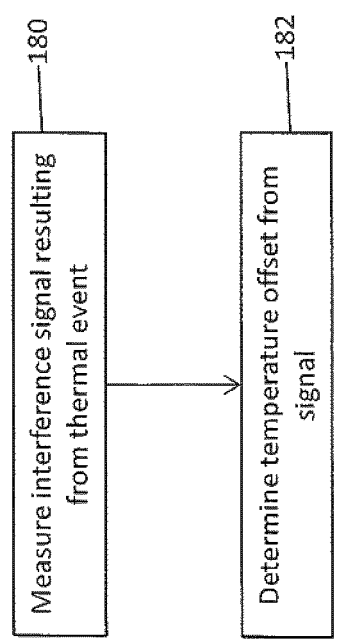
FIG. 10 is a flow chart of steps in a method using optical fiber interferometry for determining temperature offset in a region of interest.

One conventional way of determining ΔnL is by using what is broadly referred to as distributed acoustic sensing ("DAS"). DAS involves laying the fiber 112 through or near a region of interest and then sending a coherent laser pulse along the fiber 112. As shown in FIG. 10, the laser pulse interacts with impurities 113 in the fiber 112, which results in scattered laser light 117 because of Rayleigh scattering. Vibration or acoustics emanating from the region of interest results in a certain length of the fiber becoming strained, and the optical path change along that length varies directly with the magnitude of that strain. Some of the scattered laser light 117 is back scattered along the fiber 112 and is directed towards the optical receiver 103, and depending on the amount of time required for the scattered light 117 to reach the receiver and the phase of the scattered light 117 as determined at the receiver, the location and magnitude of the vibration or acoustics can be estimated with respect to time. DAS relies on interferometry using the reflected light to estimate the strain the fiber experiences. The amount of light that is reflected is relatively low because it is a subset of the scattered light 117. Consequently, and as evidenced by comparing FIGS. 1B and 1C, Rayleigh scattering transmits less light back towards the optical receiver 103 than using the FBGs 114.

DAS accordingly uses Rayleigh scattering to estimate the magnitude, with respect to time, of the event experienced by the fiber during an interrogation time window, which is a proxy for the magnitude of the event, such as vibration or acoustics emanating from the region of interest. In contrast, the embodiments described herein measure events experienced by the fiber 112 using interferometry resulting from laser light reflected by FBGs 114 that are added to the fiber 112 and that are designed to reflect significantly more of the light than is reflected as a result of Rayleigh scattering. This contrasts with an alternative use of FBGs 114 in which the center wavelengths of the FBGs 114 are monitored to detect any changes that may result to it in response to strain. In the depicted embodiments, groups of the FBGs 114 are located along the fiber 112. A typical FBG can have a reflectivity rating of 2% or 5%. The use of FBG-based interferometry to measure interference causing events offers several advantages over DAS, in terms of optical performance.

Described herein are embodiments that relate to the use of optical fiber interferometry for determining whether an interference causing event comprises a strain event or a thermal event in a region of interest. The computer readable medium 104 is encoded with program code executable by the processor 102 to carry out a method for determining whether an interference causing event comprises a strain event or a thermal event in a region of interest. The optical fiber 112 comprising pairs of FBGs 114 extends through the region of interest and pairs of the FBGs 114 on the fiber 112 delineate the region of interest into sensing zones including at least a first sensing zone and a second sensing zone having non-overlapping portions.

Figure 2:
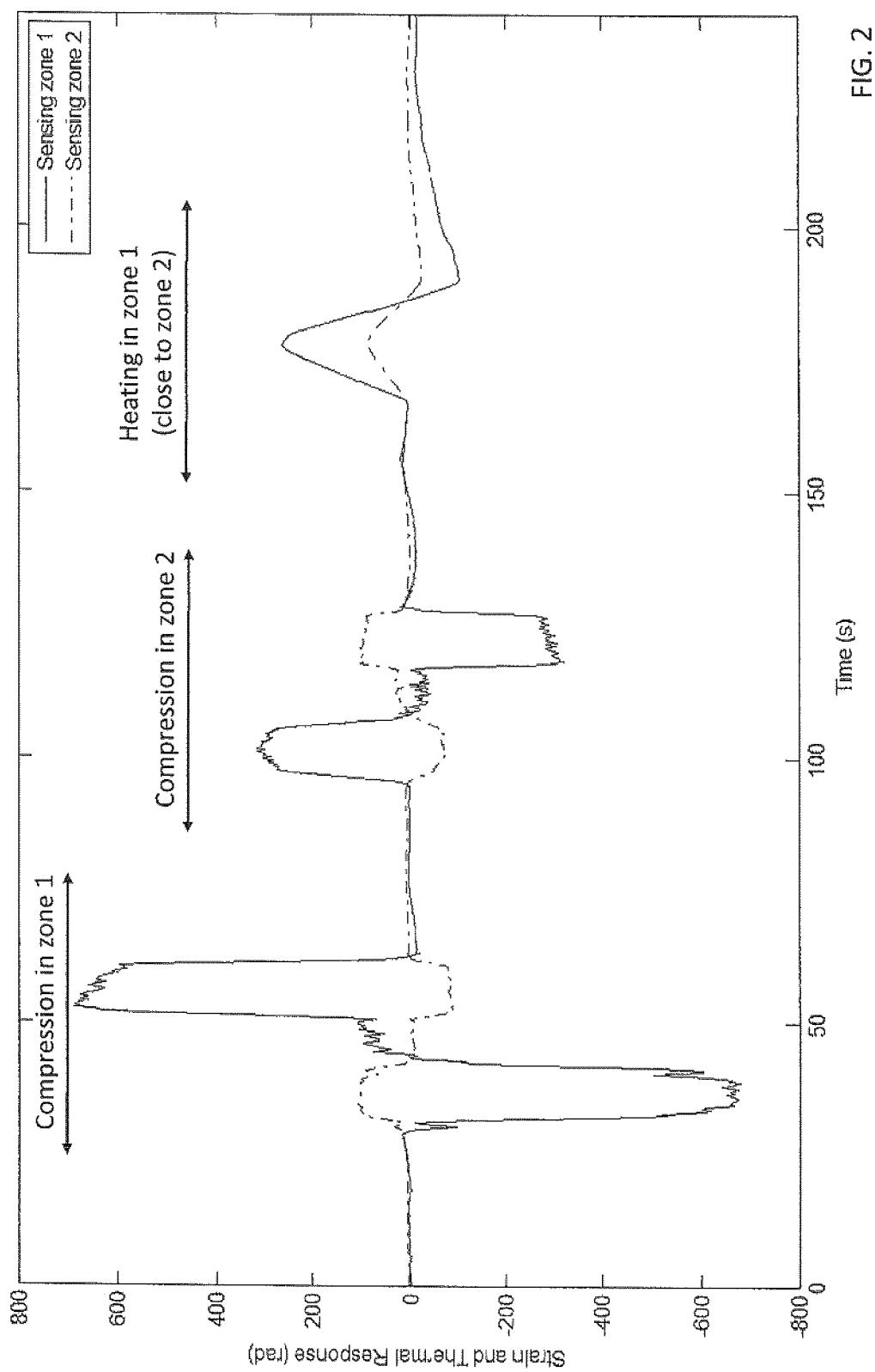
FIG. 2 is a graph of a first interference signal from a first sensing zone ("sensing zone 1") and a second interference signal from a second sensing zone ("sensing zone 2") plotted against time for different interference causing events.

FIG. 2 shows an exemplary graph of a first interference signal from the first sensing zone ("sensing zone 1") and a second interference signal from the second sensing zone ("sensing zone 2") plotted against time for different interference causing events. The initial interference causing event comprises a compression ("strain event") in sensing zone 1 which produces a negative spike followed by a positive spike in the first interference signal, and a positive spike followed by a negative spike in the second interference signal. The initial or first spike for each interference signal (positive or negative) results from variation in the length of the fiber segment 116 in response to the strain event and the subsequent or second opposite spike (negative or positive) is a result of the length of the fiber segment 116 returning to its baseline length (i.e. the length before the strain event occurs). The polarities of the first and second interference signals differ for each spike (i.e. one is positive and the other is negative). By "polarity" it is meant the direction of the delta/change of the interference signal from immediately before the interference causing event. The next interference causing event comprises a compression (strain event) in sensing zone 2 which produces a positive spike followed by a negative spike in the first interference signal, and a negative spike followed by a positive spike in the second interference signal. Again the subsequent or second spike results from the fiber segment 116 returning to its baseline length after the strain event occurs and the polarities of the first and second interference signals differ (i.e. are opposite) for each spike. The final interference causing event comprises heating ("thermal event") in sensing zone 1 close to sensing zone 2. The heating produces a positive curve in both the first and second interference signals followed by a smaller negative curve and the polarities of the first and second interference signals are the same. The initial positive curve results from variation in the length of the fiber segment 116 in response to the heating event and the subsequent negative curve results from cooling of the fiber (i.e. a return to baseline) after the heating event has been removed.

Figure 3:
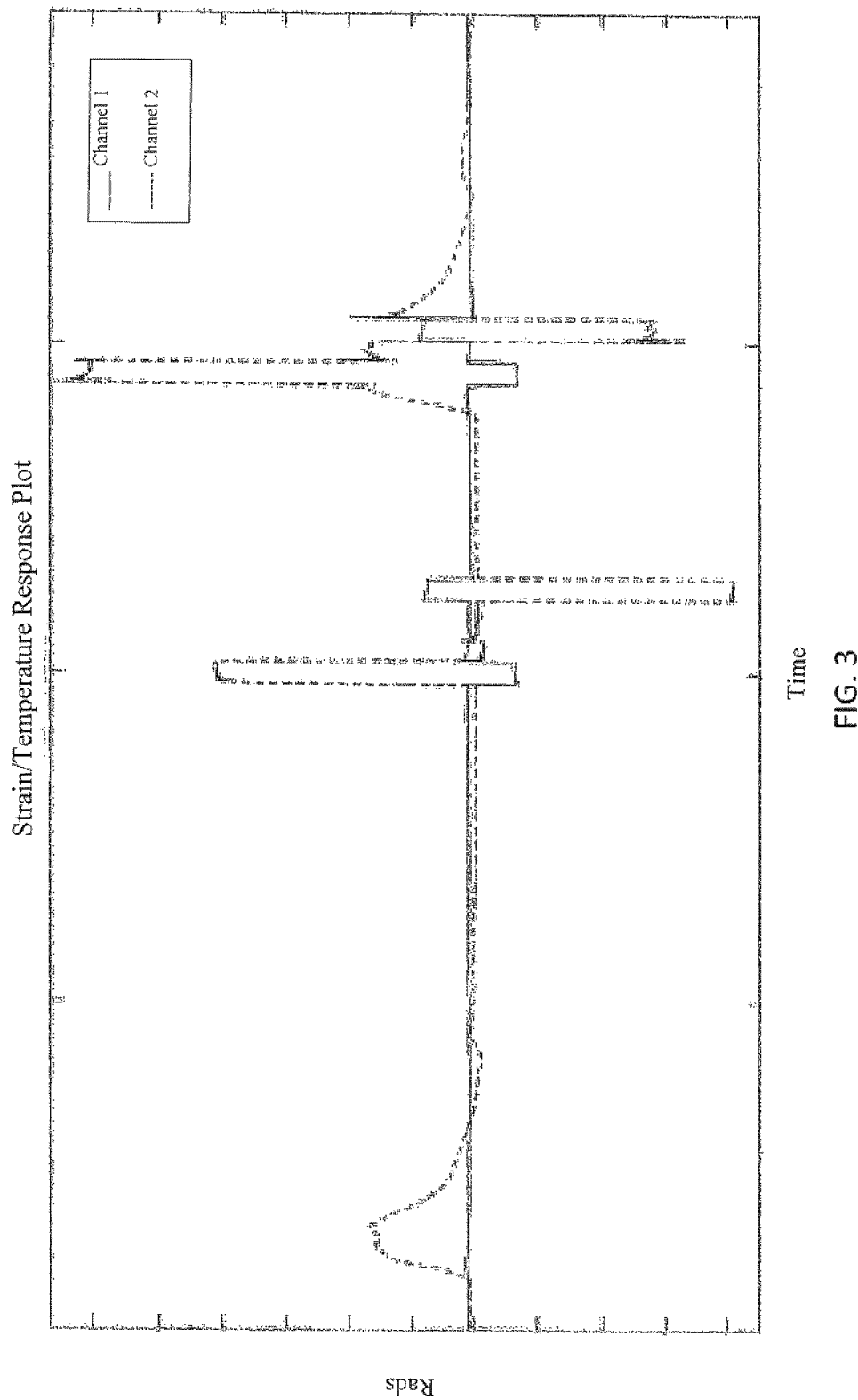
FIG. 3 is a graph of a first interference signal from a first sensing zone ("channel 1") and a second interference signal from a second sensing zone ("channel 2") plotted against time for different interference causing events.

The interference causing event may comprise a strain event, a thermal event or a thermal and strain event. FIG. 3 shows an exemplary graph of a first interference signal from the first sensing zone ("channel 1") and a second interference signal from the second sensing zone ("channel 2") plotted against time for different interference causing events. The initial interference causing event is a temperature change of about 0.1° C. (thermal event) that produces a positive curve in the second interference signal. The next interference causing event is a microstrain of about 100με (strain event) which produces a negative spike followed by a positive spike in the first interference signal, and a positive spike followed by a negative spike in the second interference signal. The polarities of the first and second interference signals differ for each spike. The final interference causing event is a 0.1° C. temperature change and a 100με microstrain (thermal and strain event) which produces a negative spike followed by a positive spike in the first interference signal. The second interference signal has a positive spike followed by a negative spike caused by the strain event superimposed with a positive curve caused by the thermal event. The polarities of the first and second interference signals differ for each spike.

By comparing the polarities of the first interference signal from sensing zone 1 and the second interference signal from sensing zone 2, the processor 102 can determine if the interference causing event comprises a strain event. When the polarities of the first and second interference signals generated by the interference causing event differ, this is indicative that the interference causing event comprises a strain event such as the compression events shown in FIG. 2 and the microstrain events shown in FIG. 3. Furthermore, the magnitude of the interference signals may be indicative of the magnitude of the strain event.

Figure 4:
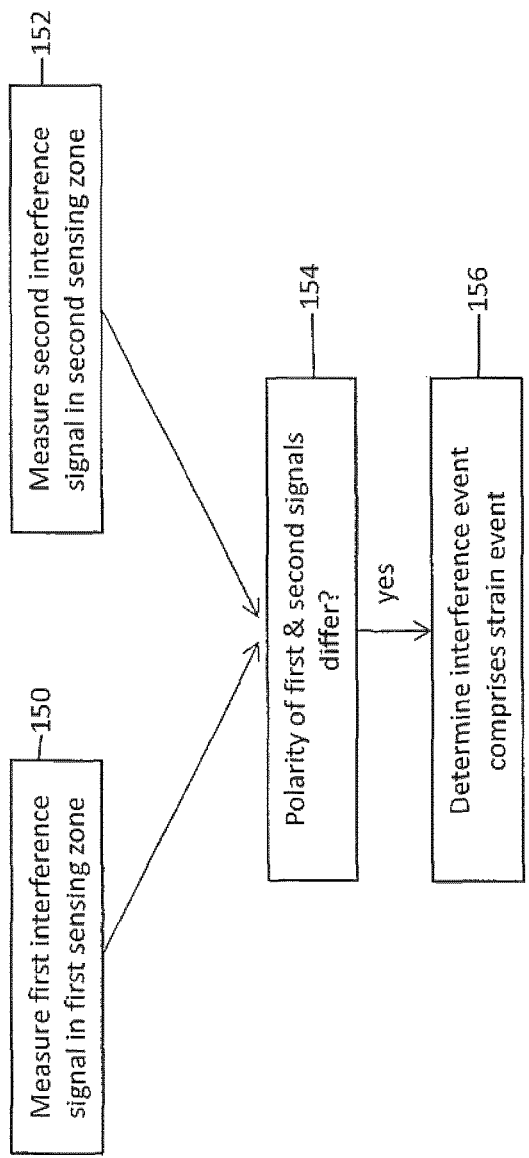
FIG. 4 is a flow chart of steps in a method using optical fiber interferometry for determining whether an interference causing event in a region of interest comprises a strain event or a thermal event, according to an embodiment.

According to one embodiment and referring to FIG. 4, the method for determining whether an interference causing event in the region of interest comprises a strain event or a thermal event includes measuring a first interference signal resulting from the interference causing event using a first pair or pairs of FBGs 114 in the first sensing zone (step 150) and measuring a second interference signal resulting from the interference causing event using a second pair or pairs of FBGs 114 in the second sensing zone (step 152). The measuring steps 150, 152 are carried out using optical fiber interferometry performed by the optical fiber 112 and the interrogator 106 digitizes the phase difference of the first and second interference signals generating first and second output interference signals as described above in more detail. The processor 102 compares the polarities of the first and second output interference signals and determines if there is a difference between the polarities of the first and second interference signals generated by the interference causing event (step 154). If the polarities of the first and second interference signals differ, then the processor 102 determines that the interference causing event comprises a strain event (step 156).

Figure 5:
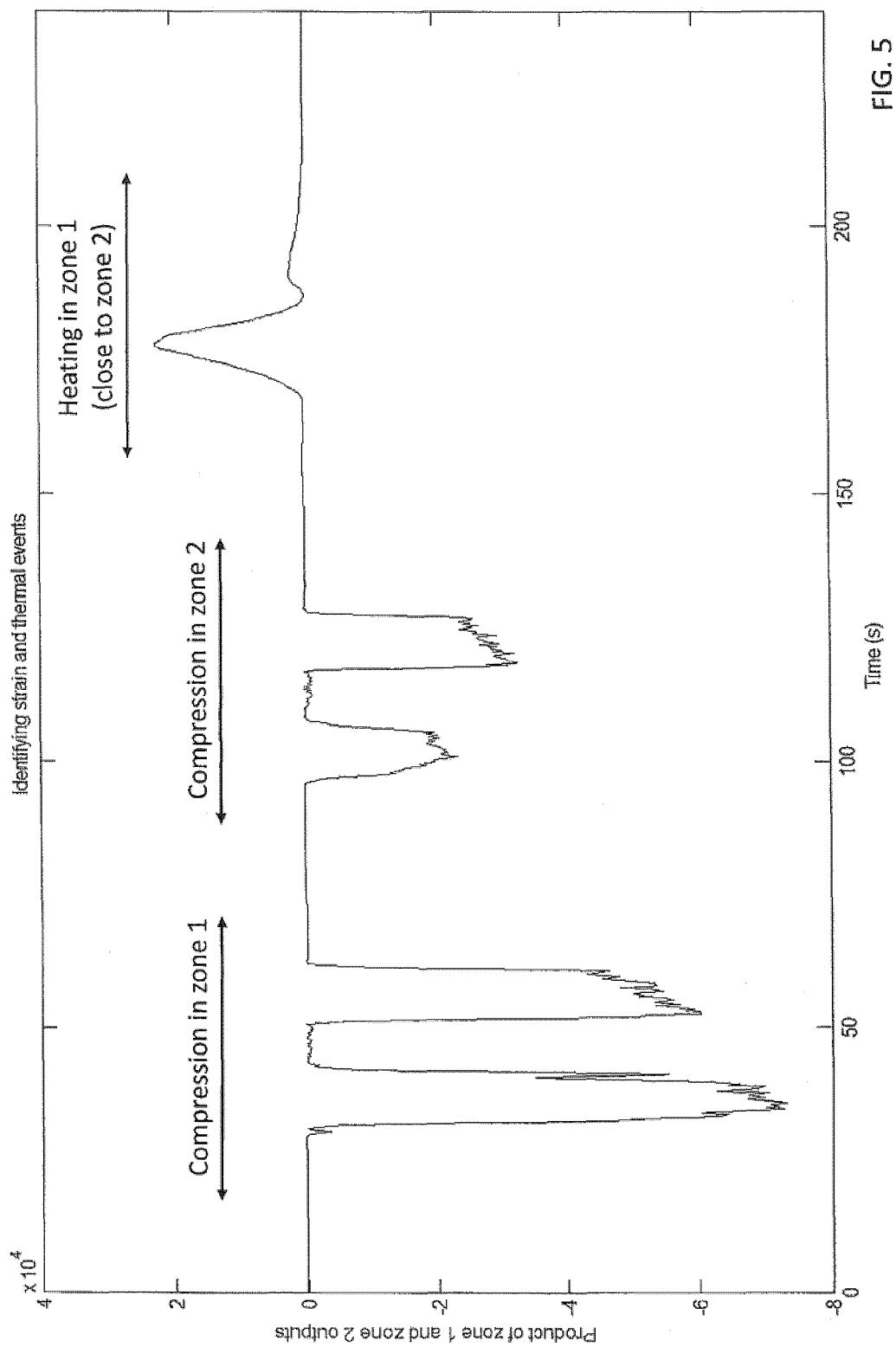
FIG. 5 is a graph showing the product of the first and second interference signals from FIG. 3 plotted against time.

Referring now to FIG. 5, the product of the first and second interference signals from FIG. 2 is plotted against time. The product of the first and second interference signals resulting from the compression (strain event) in zones 1 and 2 is negative, whereas the product of the first and second interference signals resulting from the heating (thermal event) in zone 1 is positive. Therefore the product of the first and second interference signals may be used as a means for determining if the interference causing event is a strain event.

Figure 6:
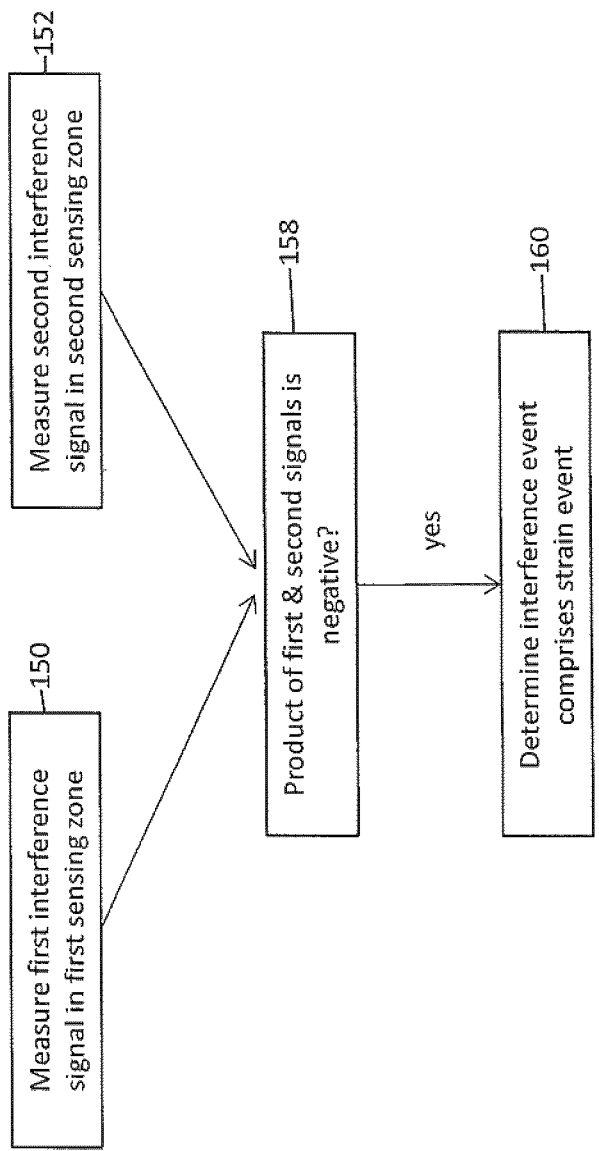
FIG. 6 is a flow chart of steps in a method using optical fiber interferometry for determining whether an interference causing event in a region of interest comprises a strain event or a thermal event, according to another embodiment.

According to another embodiment and referring to FIG. 6, the method for determining whether an interference causing event in the region of interest comprises a strain event or a thermal event includes the measuring steps 150 and 152 as described above. The processor 102 multiplies the first and second interference signals to determine if the product of the first and second interference signals is negative (step 158). If the product of the first and second interference signals is negative, then the processor 102 determines that the interference causing event comprises a strain event (step 160).

A strain event may not always cause a first interference signal from a first sensing zone to have a different polarity to a second interference signal from a second sensing zone adjacent the first sensing zone and additional sensing zones delineated by pairs of FBGs 114 may be needed for the strain event to generate interference signals that have different polarities. The number of additional sensing zones needed to generate interference signals with different polarities as a result of a strain event may depend on operating conditions, such as the composition of the fiber 112, the environment in which the fiber 112 is positioned and other factors.

Figure 7:
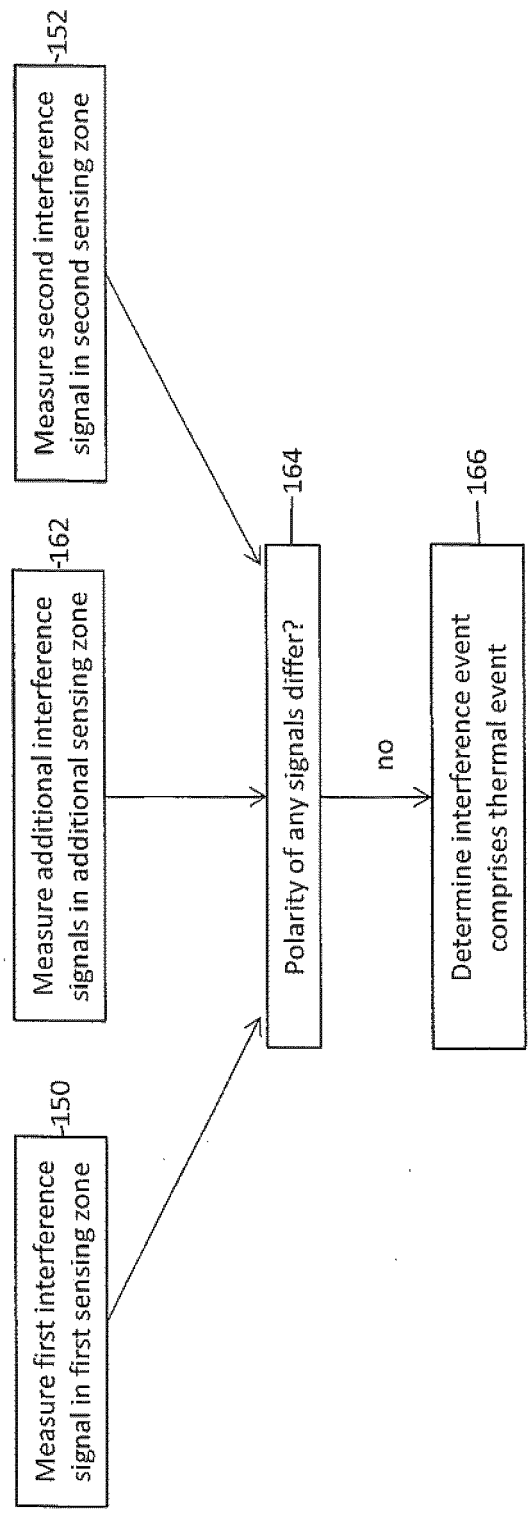
FIG. 7 is a flow chart of steps in a method using optical fiber interferometry for determining whether an interference causing event in a region of interest comprises a strain event or a thermal event, according to another embodiment.

According to another embodiment and referring to FIG. 7, the method for determining whether an interference causing event in the region of interest comprises a strain event or a thermal event includes the measuring steps 150 and 152 as described above. The method also includes measuring one or more than one additional interference signal caused by the interference causing event in one or more than one additional sensing zone by an additional pair or pairs of FBGs 114 in the one or more than one additional sensing zone (step 162). The measuring steps 150, 152, 162 are carried out using optical fiber interferometry performed by the optical fiber 112 comprising the pairs of FBGs 114, and the interrogator 106 digitizes the phase difference of the interference signals generating output interference signals as described above in more detail. The processor 102 compares the polarities of the output interference signals and determines if there is a difference between the polarities of any of the interference signals generated by the interference causing event (step 164). If the polarities of the interference signals do not differ, then the processor 102 determines that the interference causing event comprises a thermal event (step 166). The number of additional sensing zones and additional interference signals measured therefrom required to determine that the interference event is a thermal event and not a strain event may be determined based on operating conditions, such as the composition of the fiber 112, the environment in which the fiber 112 is positioned and other factors. For example, the number of additional sensing zones required may depend on the nature of the strain event (its strength, etc) and the spacing of the sensing zones. If the sensing zones are very close (i.e. high spatial resolution), then more additional sensing zones may be needed.

Figure 8:
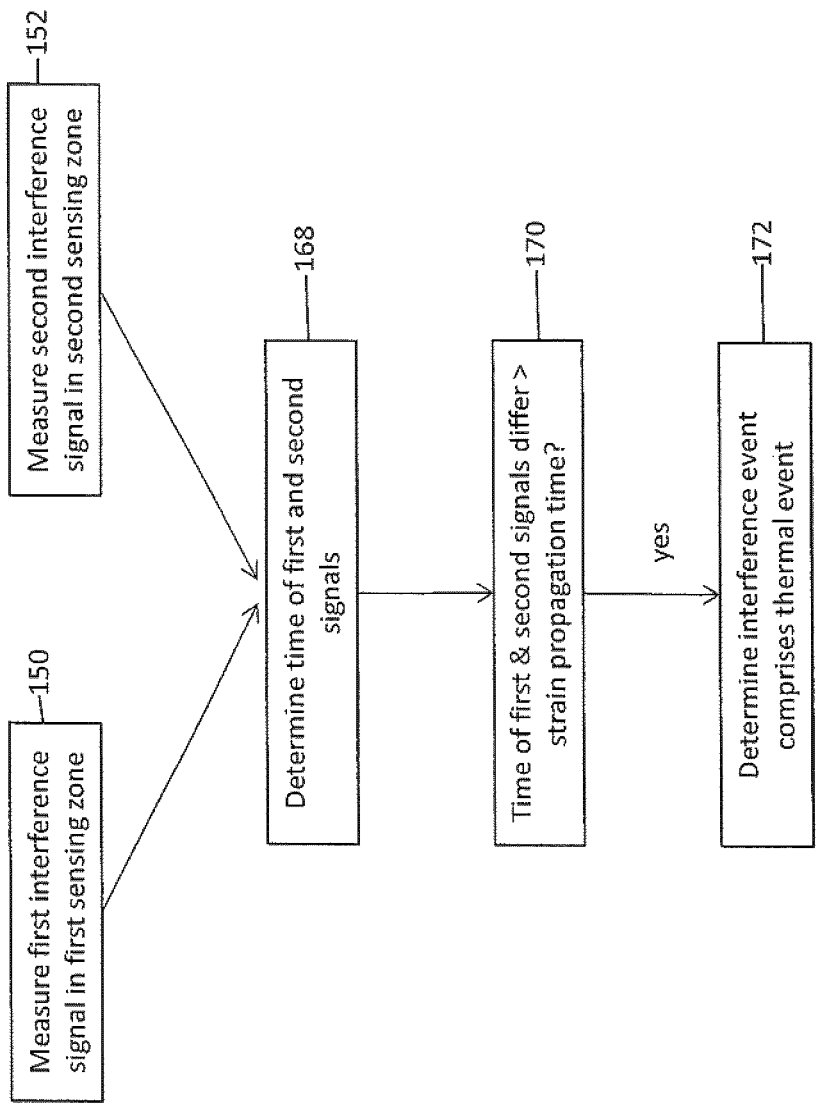
FIG. 8 is a flow chart of steps in a method using optical fiber interferometry for determining whether an interference causing event in a region of interest comprises a strain event or a thermal event, according to another embodiment.

According to another embodiment and referring to FIG. 8, the method for determining whether an interference causing event in the region of interest comprises a strain event or a thermal event includes the measuring steps 150 and 152 as described above. The computer readable medium 104 is encoded with program code executable by the processor 102 to determine a duration of time required by a strain event to propagate through one or more zones separating the first and second sensing zones ("strain propagation time"). Alternatively, the computer readable medium 104 is encoded with a predetermined strain propagation time for a given set of environmental conditions. The processor 102 determines the time at which the first and second interference signals are generated by the interference causing event (step 168) and determines if the time of the first and second interference signals differs by more than the strain propagation time (step 170). The time required for a thermal event to propagate through the zone(s) separating the first and second sensing zones ("thermal propagation time") is greater than the strain propagation time, therefore if the time of the first and second interference signals differs by more than the strain propagation time, the processor 102 determines that the interference causing event comprises a thermal event (step 172).

Optical fiber interferometry may be used to monitor changes in frequency of dynamic strain and/or to monitor changes in magnitude of dynamic strain. A change in magnitude of dynamic strain may indicate an acoustic event in a housing in which the optical fiber 112 is deployed. A change in strain magnitude can also indicate stretch, compression, elongation or shear of the housing. If the applied strain changes with time, the magnitude of the observed strain will also change in time, and a particular frequency will be observed. Optical fiber interferometry may be used to estimate where along the housing the dynamic strain is occurring. This information could be used to provide an indication of where a leak is occurring or for other applications such as geosteering, pipeline collision detection, identification of hotspots, and pig tracking as is known in the art.

Optical fiber interferometry may be used to detect and monitor dynamic strain of, or in, a variety of housings over large or small distances. For example the optical fiber 112 may be deployed in a housing for detecting dynamic strain in the housing. In addition, the optical fiber 112 (optionally in a protective casing) may be positioned outside the housing, for example within a few meters from the exterior surface of the housing. For example, the housing may be a pipeline and the optical fiber 112 with protective casing may be buried in the ground near the pipeline to detect acoustics of the pipeline. The optical fiber 112 may be buried between two pipelines (for example equidistance between both pipelines) and used to detect acoustics in both pipelines. The housing may be a vessel, such as a fluid storage vessel. Alternatively, the housing may be a conduit of any cross-sectional shape or size, for example a tubular, pipeline, or casing of an oil and gas well. Optical fiber interferometry may also be used to detect and monitor dynamic strain of a physical area over large or small distances, for example a perimeter of a building, an oil and gas well, or any area where the optical fiber 112 is deployed in the physical area being monitored.

Figure 9B:
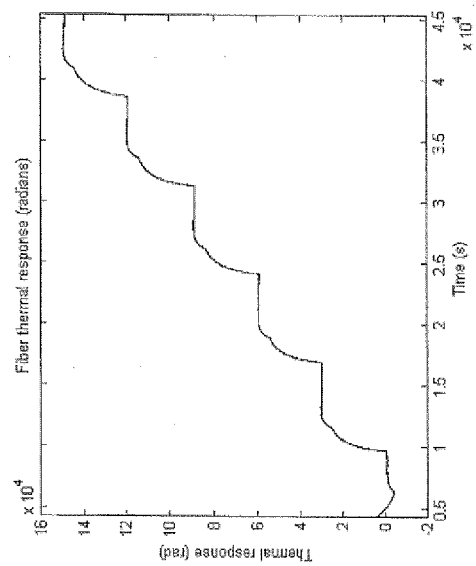
FIG. 9B is a graph of an optical fiber profile in response to thermal events in a region of interest over time.
Figure 9A:
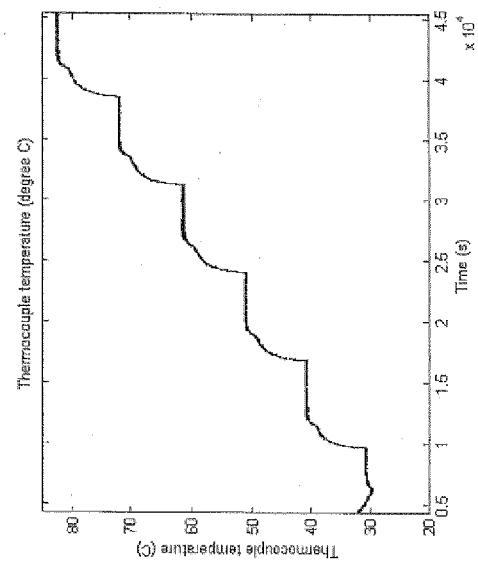
FIG. 9A is a graph of a temperature profile (° C.) measured using a thermocouple

Described herein are embodiments using optical fiber interferometry to determine temperature offset in a region of interest. In further described embodiments, the determined temperature offset is used to determine the temperature in the region of interest. FIG. 9A is a graph of a temperature profile (° C.) measured using a thermocouple in a region of interest over time. The temperature increases in stepped increments over time in response to thermal events in the region of interest. Each rising edge of the temperature profile represents a thermal event causing the temperature to increase steeply before leveling off. FIG. 9B is a graph showing an optical fiber profile in response to the same thermal events in the same region of interest over the same time period that resulted in the temperature profile shown in FIG. 9A. The optical fiber profile is based on one or more interference signals measured from the region of interest using pairs of FGBs on the optical fiber 112 as described above in more detail. The optical fiber profile may mirror the temperature profile and there may be a linear relationship between the two.

The computer readable medium 104 is encoded with program code executable by the processor 102 to carry out a method to determine the temperature offset in a region of interest using optical fiber interferometry and to carry out a method to determine the temperature in the region of interest using the determined temperature offset. The optical fiber 112 extends through the region of interest and comprises one or more than one pair of FBGs 114 with the fiber segment 116 within each pair of FBGs 114. The optical fiber 112 is within a strain insulating housing to reduce the effect of a strain event on the optical fiber 112. The strain insulating housing may comprise for example, but not limited to, a rigid steel housing, which reduces the amount of strain that is transferred from outside the housing to inside the housing. A thermal event (for example a temperature change) in the region of interest causes a change in optical path length of the fiber segment 116. According to one embodiment and referring to FIG. 10, a method for determining temperature offset in the region of interest includes measuring the interference signal resulting from change in optical path length of the fiber segment 116 (step 180). The interrogator 106 digitizes the phase difference of the interference signal generating an output interference signal as described above in more detail. The processor 102 determines a temperature offset or change in temperature (Δ° C.) in the region of interest from the output interference signal (step 182).

As discussed above, the relationship between the optical path of the fiber segment 116 and the phase difference (θ) of the output interference signal is as follows:

$$\theta = \frac{2\pi n L}{\lambda}$$

where n is the index of refraction of the optical fiber; L is the optical path length of the fiber segment 116; and 2L is the wavelength of the optical pulses. The temperature offset (Δ° C.) may be linearly related to the phase difference (θ) of the output interference signal. Temperature affects both n and L, however it generally affects n more than L. In one embodiment, the system is calibrated in order to determine the relationship between the output interference signal and Δ° C. The calibration results are recorded on the computer readable medium 104 and used by the processor 102 in step 182 to determine the temperature offset (Δ° C.) from the output interference signal generated by the thermal event.

In one embodiment, the optical fiber 112 has three or more FBGs within the region of interest and the fiber segment 116 between any two adjacent FBGs comprises one sensing zone such that there are multiple sensing zones along the optical fiber 112. A different interference signal is measured from each of the sensing zones in step 180. The temperature offset is then determined in step 182 from an average of the different interference signals. Alternatively, a different temperature offset is determined for each of the sensing zones in step 182 based on the interference signal from each sensing zone.

Figure 11:
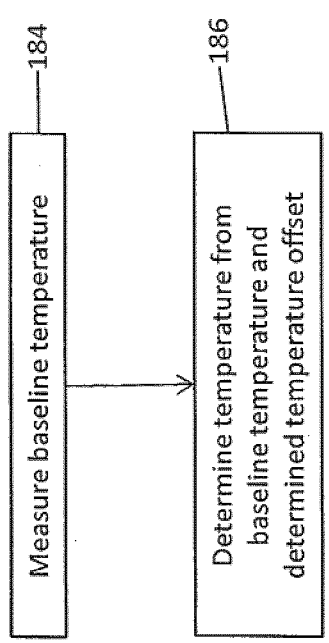
FIG. 11 is a flow chart of steps in a method using optical fiber interferometry for determining temperature in a region of interest.

According to one embodiment and referring to FIG. 11, a method to determine temperature in the region of interest using the determined temperature offset includes measuring a baseline temperature in the region of interest using non-interferometric temperature sensing. The non-interferometric temperature sensing may comprise a distributed temperature sensing system (DTS) or may be performed using a point sensor, such as a thermocouple, or the like (step 184). The baseline temperature measurement is recorded by the processor 102. The temperature offset in the region of interest is determined using optical fiber interferometry as discussed above with reference to FIG. 10. The processor 102 then determines the temperature in the region of interest from the baseline temperature and the determined temperature offset (step 186).

In embodiments where there are multiple sensing zones along the optical fiber 112 in the region of interest, different baseline temperatures for each of the sensing zones may be measured in step 184 using the non-interferometric temperature sensing device. The baseline temperature used to determine the temperature in step 186 may be an average of the different baseline temperatures. Alternatively, a different temperature for each sensing zone may be determined in step 186 based on the baseline temperature and the determined temperature offset for each sensing zone.

It is contemplated that any part of any aspect or embodiment discussed in this specification can be implemented or combined with any part of any other aspect or embodiment discussed in this specification.

For the sake of convenience, the exemplary embodiments above are described as various interconnected functional blocks. This is not necessary, however, and there may be cases where these functional blocks are equivalently aggregated into a single logic device, program or operation with unclear boundaries. In any event, the functional blocks can be implemented by themselves, or in combination with other pieces of hardware or software.

While particular embodiments have been described in the foregoing, it is to be understood that other embodiments are possible and are intended to be included herein. It will be clear to any person skilled in the art that modifications of and adjustments to the foregoing embodiments, not shown, are possible.

The invention claimed is:

1. A method for using optical fiber interferometry to determine whether an interference causing event comprises a strain event or a thermal event in a region of interest, the method comprising:
    (a) measuring, in a first zone in the region of interest, a first signal resulting from the interference causing event, wherein the first signal is measured using optical fiber interferometry performed using an optical fiber comprising fiber Bragg gratings (FBGs) that extends through the region of interest and wherein pairs of the FBGs delineate the region of interest into at least the first zone and a second zone having non-overlapping portions;
    (b) measuring in the second zone a second signal resulting from the interference causing event, wherein the second signal is measured using the optical fiber interferometry performed using the optical fiber;
    (c) comparing the polarities of the first and second signals; and
    (d) when the polarities of the first and second signals differ, determining that the interference causing event comprises the strain event.

2. The method of claim 1, further comprising determining the product of the first and second signals and determining that the interference causing event comprises the strain event when the product of the first and second signals is negative.

3. The method of claim 1 wherein the FBGs delineate the region of interest into at least three zones, and wherein the first and second zones are separated by at least another of the zones.

4. The method of claim 3 further comprising measuring a time of the first and second signals and determining that the interference causing event comprises the thermal event when the times at which the first and second signals are measured differ by more than a strain propagation time, wherein the strain propagation time comprises a duration of time required by the strain event to propagate through the at least another of the zones separating the first and second zones.

5. The method of claim 1 wherein the FBGs delineate the region of interest into at least three zones, and wherein the first and second zones are adjacent to each other.

6. The method of claim 1 wherein the FBGs delineate the region of interest into at least three zones, and wherein the method further comprises:
    (a) measuring, in each of all remaining zones along the region of interest, additional signals resulting from the interference causing event, wherein each of the additional signals is measured using the optical fiber interferometry performed using the optical fiber; and
    (b) when the polarities of none of the signals differ, determining that the interference causing event comprises the thermal event.

7. A system for determining whether an interference causing event comprises a strain event or a thermal event in a region of interest, the system comprising:
    (a) an optical fiber comprising fiber Bragg gratings (FBGs) for extending through the region of interest, wherein pairs of the FBGs delineate the region of interest into at least a first zone and a second zone having non-overlapping portions;
    (b) an interrogator comprising a laser source and a photodetector, wherein the interrogator is configured to perform optical fiber interferometry by shining laser light along the optical fiber and detecting light reflected by the FBGs; and (c) a controller operative to:
  (i) measure in the first zone a first signal resulting from the interference causing event, wherein the first signal is measured using the optical fiber interferometry;
  (ii) measure in the second zone a second signal resulting from the interference causing event, wherein the second signal is measured using the optical fiber interferometry;
  (iii) compare the polarities of the first and second signals; and
  (iv) determine that the interference causing event comprises the strain event when the polarities of the first and second signals differ.

8. The system of claim 7 wherein the controller is further operative to:
  (i) determine the product of the first and second signals; and
  (ii) determine that the interference causing event comprises the strain event when the product of the first and second signals is negative.

9. The system of claim 7 wherein the FBGs delineate the region of interest into at least three zones, and wherein the first and second zones are separated by at least another of the zones.

10. The system of claim 9 wherein the controller is further operative to:
  (i) measure a time of the first and second signals; and
  (ii) determine that the interference causing event comprises the thermal event when the time of the first and second signals differ by more than a strain propagation time,
  wherein the strain propagation time comprises a duration of time required by the strain event to propagate through the at least another of the zones separating the first and second zones.

11. The system of claim 7, wherein the FBGs delineate the region of interest into at least three zones, and wherein the first and second zones are adjacent to each other.

12. The system of claim 7, wherein the FBGs delineate the region of interest into at least three zones, and wherein the controller is further operative to:
  (i) measure, in each of all remaining zones along the region of interest, additional signals resulting from the interference causing event, wherein each of the additional signals is measured using the optical fiber interferometry; and
  (ii) determine that the interference causing event comprises the thermal event when the polarities of none of the signals differ.

\* \* \* \* \*